United States Patent [19]

Morgan

[11] Patent Number: 5,270,172
[45] Date of Patent: Dec. 14, 1993

[54] METHOD TO PREDICT TUMOR RESPONSE TO THERAPY

[75] Inventor: Lee R. Morgan, New Orleans, La.

[73] Assignee: Dekk-Tek, Inc., New Orleans, La.

[21] Appl. No.: 692,240

[22] Filed: Apr. 26, 1991

[51] Int. Cl.$^5$ .............. C12Q 1/02; C12Q 1/18; A01N 1/02; C12N 5/00

[52] U.S. Cl. .................................. 435/29; 435/2; 435/32; 435/240.2; 436/501

[58] Field of Search .................. 435/29, 2, 240.2, 32; 436/501

[56] References Cited

U.S. PATENT DOCUMENTS

| | | | |
|---|---|---|---|
| 3,726,764 | 8/1971 | White | 195/127 |
| 4,465,676 | 8/1984 | Hochberg | 424/238 |
| 4,732,904 | 3/1988 | Morgan | 514/357 |

OTHER PUBLICATIONS

Vescio et al., "In vivo-like Drug Responses of Human Tumors Growing in Three-Dimensional Gel-Supported Primary Culture", Proc. Natl. Acad. Sci. U.S.A., 84:5029–5033, (Jul. 1987).

Fan et al., "Comparison of Antitumor Activity of Standard and Investigational Drugs at Equivalent Granulocyte-Macrophage Colony-forming Cell Inhibitory Concentrations in the Adhesive Tumor Cell Culture System: An in vitro Method of Screening New Drugs", Eur. J. Cancer Clin. Oncol., 23:1469–1476 (1987).

Tueni et al., "In Vitro Activity of Bleomycin, Tallysomycin S10b, and Liblomycin Against Fresh Human Tumor Cells", Cancer Research, 49:1099–1102 (Mar. 1989).

Watanabe et al., "In Vitro Sensitivitiy Test of Breast Cancer Cells to Hormonal Agents in a Radionucleotide-Incorporation Assay", Japanese Journal of Cancer Research, 81:536–543 (May 1990).

Coezy et al., Cancer Research, 42, pp. 317–323.

Primary Examiner—Douglas W. Robinson
Assistant Examiner—Jane A. Williams
Attorney, Agent, or Firm—Klarquist, Sparkman, Campbell, Leigh & Whinston

[57] ABSTRACT

A method is disclosed for predicting response of a tumor patient to therapy, and selecting appropriate therapy for malignant neoplasms such as breast, ovarian and gastrointestinal cancer. A sample of tumor cells is cultured in the presence of 10 μg/ml estradiol, and inhibition of cell growth in the culture paradoxically indicates an estrogen dependent tumor that will respond to antiestrogenic therapy. Another sample of tumor cells is cultured in the presence of a chemotherapeutic agent which predicts response of the tumor to in vivo administration of a cytotoxic agent. The chemotherapeutic agent is preferably a cytotoxic drug, or a drug having both cytotoxic and antiestrogenic mechanisms of action. A particularly suitable substance having both mechanisms of action is:

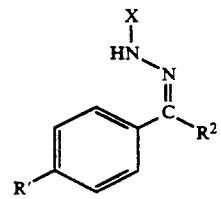

wherein $R^1$ H, OH, OOC(CH$_2$)$_2$CO$_2$H or CH$_3$COO; $R^2$ is C$_6$H$_4$OH, C$_6$H$_4$OCOCH$_3$, C$_6$H$_4$OOC(CH$_2$)CO$_2$H, or C$_6$H$_5$; and X is C$_6$H$_3$-2,4(NO$_2$)$_2$, C$_6$H$_5$, C$_6$H$_4$-4(NO$_2$), C$_6$H$_4$-3(NO$_2$), or C$_6$H$_3$-2,4(NO$_2$)$_2$;

Predictive power of the assay is increased by combining information from the estradiol and chemotherapeutic assays. These assays are preferably performed in culture flasks having removable bases that function as conventional microscope slides.

10 Claims, 1 Drawing Sheet

METHOD TO PREDICT TUMOR RESPONSE TO THERAPY

BACKGROUND OF THE INVENTION

Field of the Invention

This invention concerns the testing of tumor cells for their sensitivity to estrogens and hydrazones. More specifically, it concerns a method and test kit useful in selecting an appropriate treatment for cancer, and predicting the probable response of a patient to therapy.

Discussion of the Background of the Invention

Approximately 55% of all human breast cancers and 20% of ovarian cancers are considered to be estrogen dependent. These tumors require an estrogen for growth, and contain cells that bind estrogens through an absorption and transport mechanism that facilitates the entry of estrogens into the cell. The absorption and transport mechanism is believed to be an estrogen receptor (ER), which is a protein that originates in the cytoplasm of the cell and initially interacts with extracellular estrogen in the cell membrane. After interacting with the estrogen, the ER folds over the estrogen to complete the tertiary structure of the receptor complex. This structural change stimulates translocation of the receptor-estrogen complex through the pores of the nuclear membrane. Once inside the nucleus, the estrogen binds to DNA and helps direct the activity of the cell.

Estrogen receptors are believed to play an important biological role in several types of hormone sensitive cancers, such as some breast and ovarian tumors, in which estrogens are essential for continued cell growth. Some therapeutic modalities take advantage of this hormone dependence by surgically removing a patient's ovaries or adrenal glands to reduce endogenous production of estrogen. Some anti-cancer drugs also take advantage of the hormone dependence of these cells. Tamoxifen and certain nitrophenylhydrazones, for example, have an antiestrogenic activity that interferes with the interaction between the ER and endogenous estrogen. This interference prevents estrogen incorporation into the cell, and can inhibit growth of estrogen dependent tumor cells.

The prognostic importance of a patient's estrogen receptor status is illustrated by the significantly improved treatment outcome seen in patients who are ER+. It has been found, for example, that approximately 50-70% of ER+ patients respond to endocrine manipulations or antiestrogenic therapy, while ER− patients have a response rate between 0% and 10%. Patients with ER+ tumors also tend to have a better prognosis with lower recurrence rates and a longer disease-free interval.

In addition to ER status, it has been found that the presence or absence of a progesterone receptor (PgR) in the tumor cells helps select those ER+ patients who are most likely to respond to endocrine treatment. The presence of PgR and ER together appears to be a better indicator of a favorable treatment outcome than ER values alone. PgR is detected in approximately two-thirds of ER+ tumors, and is only occasionally found in ER− tumors. Its presence has been shown to improve the prediction of an objective response to endocrine therapy.

The use of quantitive methods to detect and quantitate estrogen and progesterone receptors has provided one basis for prescribing antiestrogens and other hormone manipulation therapies to treat patients with hormone dependent malignancies. Ligand binding assays, monoclonal antibody assays, and enzyme immunochemical analyses have been used to detect and quantitate these receptors, as disclosed in *ACTA Oncologica*, 27:1-19 (1988). Using such techniques, it has been determined that breast cancer tissue containing ER concentrations greater than 5 fentomoles/ng and PgR concentrations greater than 3 fentomoles/ng is considered sensitive to antiestrogen therapy (*J. Clinical Oncology*, 1:227-241 (1985)). The higher the ER/PgR concentrations, the more sensitive the tissue should be to the antiestrogen therapy.

Unfortunately, a tumor's ER and PgR status is not always useful in predicting a response to endocrine therapies. The insensitivity of receptor screening is even more pronounced with respect to predicting response to non-hormonal chemotherapeutic agents, such as doxorubicin, methotrexate or 5-fluorouracil. In the ER−/PgR− case, for example, one can conclude that the tumor will probably not respond to hormonal therapy, but these results give no guidance about the likelihood of response to non-hormonal chemotherapy. When the tumor is ER+/PgR−, some response to antiestrogens is expected, but only about 30% of the tumors will respond to such therapy. Finally, even patients who are ER+/PgR+ may fail to respond to antiestrogenic therapy, especially if the quantitative level and cell distribution of receptors is low. These problems illustrate that hormone receptor status alone is often inadequate in selecting appropriate treatment or predicting outcome of chemotherapy in patients with breast cancer.

Efforts have been made to develop in vitro tests of cell sensitivity that would avoid such problems by predicting in vivo responses of tumors to chemotherapeutic drugs. Vescio et al., for example, described a three dimensional, gel-supported culture system for growing human tumors in the presence of a variety of different cytotoxic drugs to predict differential drug sensitivities of multiple cell types within individual cultured tumors. *Proc. Natl. Acad. Sci.*, 84:5029-5033 (1987). In vitro tests for predicting response to hormonal agents, however, have been found to be particularly unhelpful. Wantanabe et al., *Japanese Journal of Cancer Research*, 81:536-43 (1990). In addition, such in vitro assays have typically monitored cell division and growth to determine cell viability with time. These assays are laborious procedures designed to select the most effective drugs to stop the cells from replicating and growing. As many as twenty drugs are often required in such assays to provide a productive profile of drug sensitivities for any one cancer tissue.

Hence, a need still exists for a relatively rapid, simple and efficient in vitro method of predicting a patient's response to chemotherapy and other modalities of treatment.

Therefore, it is one object of the present invention to provide an efficient test system to determine drug sensitivities of living cancer cells, and predict responses of cancer patients to hormonal therapies.

It is yet another object of the present invention to provide such an improved test system to determine sensitivities of cancer cells to non-hormonal chemotherapy, and predict patient response to a variety of non-hormonal chemotherapeutic agents.

Yet another object of the invention is to provide an efficient, cost-effective in vitro prognosticative assay for predicting probable response of patients to medical and surgical intervention.

These and other objects of the invention will be understood more clearly by reference to the following detailed description and drawing.

SUMMARY OF THE INVENTION

The foregoing objects are achieved by providing a method of predicting in vivo response of tumor cells to therapy by culturing a sample of the cells in the presence of a cancer chemotherapeutic drug and quantitating the degree of inhibition of cell growth in the cultured sample. The drug is preferably a nitrophenylhydrazone such as:

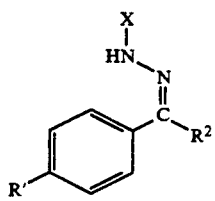

wherein $R^1$ is hydrogen, hydroxy, acetate, succinate or another water soluble group; $R^2$ is $C_6H_4OH$, $C_6H_4OCOCH_3$, $C_6H_4OCO(CH_2)CO_2H$ or $C_6H_5$; and X is $C_6H_3$-2,4$(NO_2)_2$, $C_6H_5$, $C_6H_4$-4$(NO_2)$, $C_6H_4$-3$(NO_2)$, or $C_6H_3$-2,4$(NO_2)_2$. In especially preferred embodiments, $R^1$ is OH, $R^2$ is $C_6H_4OH$ and X is $C_6H_3$-2,4$(NO_2)_2$. These hydrazones have been found to have both cytotoxic and antiestrogenic mechanisms of action.

When assaying cells that may be hormone dependent, such as breast or ovarian tumor cells, a first sample of the cells may be cultured in the presence of a sufficient amount of an estrogen to inhibit growth of estrogen sensitive cells in the culture. A second sample of the cells is cultured in the presence of a chemotherapeutic agent that, when cultured with a sample of the tumor cells, predicts a patient's probable response to therapeutic interventions. The degree of inhibition of cell growth in each cultured sample is determined, which allows selection of a treatment modality based on the degree of inhibition of cell growth. Specifically, an antiestrogen therapy is selected if the degree of inhibition of cell growth in the presence of estrogen is significant. A non-hormonal therapy is indicated if cell growth in the estrogen-containing first sample is stimulated or not inhibited. In the latter case, if an $IC_{50}$ is noted at lower concentrations ($\leq 10$ $\mu g/ml$) of the hydrazone, sensitivity to a cancer chemotherapies is suggested. If the cell growth is inhibited only at higher concentrations of the hydrazone in the second culture, the patient will probably not improve when given either hormonal or non-hormonal therapy.

The invention also includes a test kit designed to help select treatment for cancer patients or predict probable response of a patient to a proposed therapy. The kit includes a control culture container, and a culture container for a chemotherapeutic agent that predicts a patient's probable therapeutic response to therapeutic interventions when cultured with a sample of the tumor cells. In preferred embodiments, the chemotherapeutic agent is a nitrophenylhydrazone, particularly 4,4'-dihydroxydiphenyl-methylene-2,4-dinitrophenylhydrazone (A-007), which has been found to predict response to chemotherapy. Tumor cells are cultured in the presence of the agent, and cell growth is compared to control culture growth to determine the relative degree of inhibition of tumor cell growth in the presence of the agent.

The kit preferably includes a plurality of culture flasks that are provided with a supply of different amounts of the agent to assess the concentration of drug at which an $IC_{50}$ is observed. In the disclosed embodiment, three culture flasks respectively contain 10, 15 and 20 $\mu g/ml$ of A-007. Tumor cells are cultured in each of these flasks, and cell growth is compared to growth in the control culture medium flask. A significant advantage may be obtained by using A-007, because a particularly strong correlation has been observed between the $IC_{50}$ in the presence of A-007 and the response of a patient to both hormonal and non-hormonal cancer therapies.

Alternatively, the kit can include a culture flask that contains an estrogen, such as 10 $\mu g/ml$ of estradiol. Tumor cells are cultured in the presence of estradiol, and cell growth is compared to growth in a control culture medium flask. Paradoxically, estrogen dependent tumors (such as those having high levels of estrogen receptors) will exhibit growth inhibition in the presence of this supraphysiological amount of estradiol. Equally unexpectedly, growth of non-estrogen dependent tumor cells is unaffected or stimulated.

A particularly powerful degree of prognostication is achieved by combining the results of the separate tumor cell culture growths in the presence of estradiol and in the presence of the chemotherapeutic agent.

DETAILED DESCRIPTION OF PREFERRED EMBODIMENTS

Figure 1:
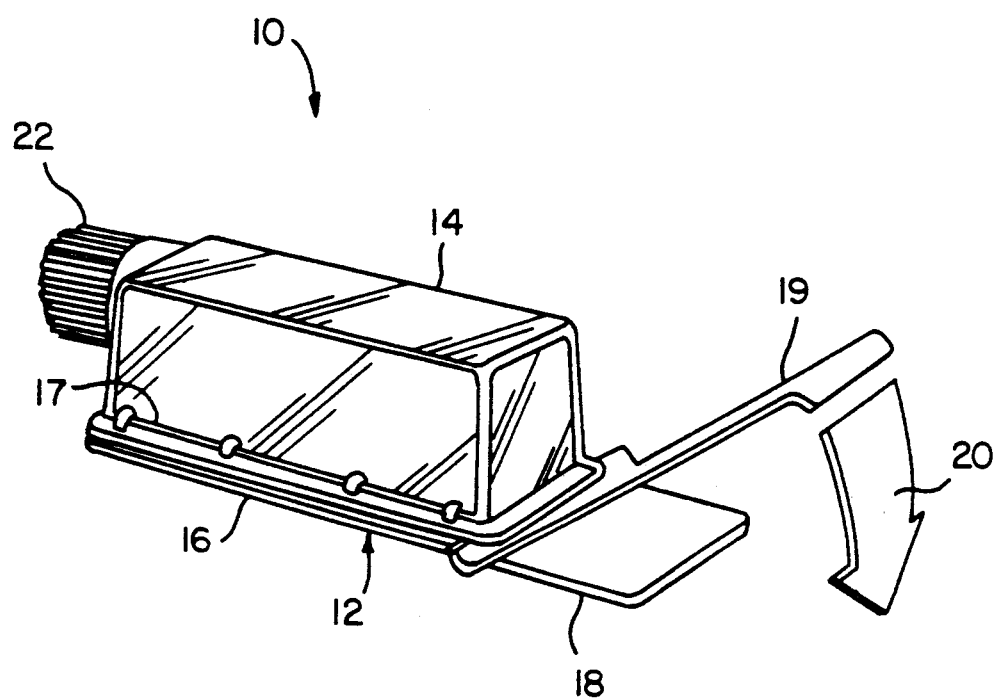
FIG. 1 is a top perspective view of a culture flask useful in performing the method of the present invention.

The in vitro assay of the present invention provides a relatively simple test that increases the effectiveness with which appropriate therapy can be selected for a cancer patient. The assay also provides prognostic information that is not presently available from quantitative assays for estrogen and progesterone receptors alone. In its simplest embodiments, the assay exposes tumor cells in culture to a substance that, when cultured with a sample of the tumor cells, predicts a patient's probable response to proposed therapies. The substance is preferably an antiestrogenic hydrazone such as:

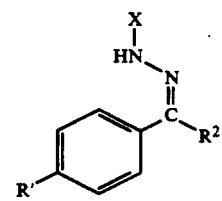

wherein $R^1$ is H, OH, $CH_3COO$, or $HO_2C(CH_2)_2COO$; $R^2$ is $C_6H_4OCOCH_3$, $C_6H_4OOC(CH_2)_2CO_2H$ or $C_6H_5$; and X is $C_6H_3$-2,4$(NO_2)_2$, $C_6H_5$, $C_6H_4$-4$(NO_2)$, $C_6H_4$-3$(NO_2)$, or $C_6H_3$-2,4$(NO_2)_2$. In especially preferred embodiments, $R^1$ is OH, $R^2$ is $C_6H_4OH$ and X is $C_6H_3$-2,4$(NO_2)_2$.

Several examples of these hydrazones are set forth below:

TABLE I
Antiestrogenic Hydrazones

| Compound | $R^1$ | $R^2$ | X |
|---|---|---|---|
| A-007 | HO | $C_6H_4OH$ | $C_6H_3$-2,4$(NO_2)_2$ |
| A-070 | HO | $C_6H_4OH$ | $C_6H_5$ |
| A-100 | HO | $C_6H_4OH$ | $C_6H_4$-4$(NO_2)$ |
| A-034 | HO | $C_6H_4OH$ | $C_6H_4$-3$(NO_2)$ |
| A-032 | $CH_3COO$ | $C_6H_4OCOCH_3$ | $C_6H_3$-2,4$(NO_2)_2$ |
| A-033 | H | $C_6H_5$ | $C_6H_3$-2,4$(NO_2)_2$ |
| A-106 | $HO_2C(CH_2)_2COO$ | $C_6H_4$-OOC$(CH_2)_2CO_2H$ | $C_6H_3$-2,4$(NO_2)_2$ |

The structures and methods of synthesis for these compounds have already been described in U.S. Pat. No. 4,732,904, for A-007 (4,4'-dihydroxydiphenylmethylene-2,4-dinitrophenylhydrazone); A-100 (4,4'-dihydroxydiphenyl-methylene-4-nitrophenylhydrazone); and A-033 (diphenyl-methylene-2,4-dinitrophenylhydrazone). U.S. Pat. No. 4,732,904 is incorporated herein by reference.

The synthesis of A-032 (4,4'-dihydroxybenzophenone phenylhydrazone) was performed by dissolving 0.389 (0.0072 mole) ammonium chloride, 4.28 g (0.02 mole) 4,4'-dihydroxybenzophenone and 6.48 g (0.06 mole) phenylhydrazine in 50 ml water. The mixture was refluxed for 48 hours. The reaction mixture was cooled and the tan solid product filtered. Light tan crystals (1.38 g) were recrystallized from 50% ethanol, m.p. 183-185°.

Analytical calculation for $C_{19}H_{16}N_2O_2$ was C, 74.98; H, 5.30.

Found: C, 75.07; H, 5.29.

The use of the invention is illustrated in the following Examples:

EXAMPLE I

Samples (1 cm) of sterile fresh human cancer tissue are obtained from a surgical biopsy or resection. The tissue can be stored in 20-50 cc RPMI-1640 tissue culture medium (Gibco Laboratories) at 5°-10° C. for up to five days. The specimen(s) are transferred under sterile conditions to a laboratory where, under sterile conditions, the tissue is removed from the holding solution and is minced by scalpel and scissors. A cellular suspension is made by cutting the specimen into 0.1 mm fragments in petri dishes of 60 ml RPMI-1640 (Gibco Laboratories) containing 10% fetal bovine serum (FBS) (Gibco Laboratories), 100 μg/ml streptomycin (Sigma Chemical Co.) and 100 units/ml penicillin (Sigma Chemical Co.).

One (1) ml of the cellular suspension is added to each of ten (10) NUNC SlideFlasks which are available from Nunc, Inc. (Catalog No. 170920 or Flask Style 177453). These flasks are described more fully in U.S. Pat. No. 3,726,764 which is incorporated herein by reference. Such a flask 10 is shown in accompanying FIG. 1 to include a baseplate 12 and a housing 14 having a 9 cm² rectangular horizontal cross section and a square vertical cross section about 2 cm in height. Housing 14 covers a 9 cm²/culture area 16 of baseplate 12, leaving a portion 18 of the baseplate protruding beyond the area covered by the housing. The bottom edge of housing 14 is sealed to baseplate 12 by a thermoplastic or adhesive seal which is substantially fluid impervious.

A flange 17 projects outwardly from the sidewalls of housing 14 spaced from and parallel to baseplate 12. The seal between the bottom edge of the housing and the baseplate can be selectively broken by prying baseplate 12 away from housing 14, for example, by inserting a lever such as opener 19 below flange 17 and prying the housing away from the base by exerting pressure on opener 19 in the direction shown by arrow 20. Once the baseplate 12 is removed from the housing, the baseplate acts as a conventional microscope slide that can be handled by portion 18 and examined under a microscope.

Near the center of a square vertical sidewall of housing 14 is an opening surrounded by a cylindrical, externally threaded neck. The threads on the neck are configured to engage internal threads of a cap 22 such that access can be selectively obtained to the interior of housing 14 by unscrewing cap 22 from the neck. Culture media and additives are introduced through the open neck, and the flask is then re-sealed by threading cap 22 back on the threaded neck.

The SlideFlask is used as an ordinary small-size culture flask with a culture area of 9 cm². After culturing, the bottom of the flask (the slide) may be removed at any step in the preparation procedure (fixation, staining, etc.), by using the SlideFlask opener a shown in FIG. 1. The bottom of the flask has standard slide microscopy dimensions and is handled exactly as a standard microscopy slide. Employing light microscopy, the cell growth on each slide is counted.

EXAMPLE II

Using A-007 as the test hydrazone, the assay consists of two flasks each labelled:
A. Control
B. Estradiol ($E_2$) (10 μg/ml)
C. A-007 (10 μg/ml)
D. A-007 (15 μg/ml)
E. A-007 (20 μg/ml)

The cellular suspension of tumor in each flask is diluted as described below.

Flasks A are diluted to 6 ml each with RPMI-1640 containing 10% FBS, 100 μg/ml streptomycin and 100 units/ml penicillin.

Flasks B are diluted to 6 ml with the same culture medium as in Flasks A, but which additionally contain estradiol (Sigma Chemical Co.) in a concentration of 10 μg/ml in the culture medium.

Flasks C are similarly diluted to 6 ml with RPMI-1640 plus FBS, penicillin and streptomycin as in flasks A, but the culture medium also contains A-007 (10 μg/ml).

Flasks D are diluted to 6 ml with RPMI-1640 plus FBS, penicillin and streptomycin as in flasks A, but the culture medium also contains A-007 (15 μg/ml).

Flasks E are diluted to 6 ml with RPMI-1640 plus FBS, penicillin and streptomycin as in flasks A, but the culture medium also contains A-007 (20 μg/ml).

The flasks are incubated for seven (7) to twenty-one (21) days in a 5% $CO_2$ incubator at 37° C. The cells may need to be cultured for a longer time to obtain sufficient cell numbers to count. Sufficient cell growth is arbitrarily said to be present in this example when at least 10 cells/HPF or ten clumps of cell/HPF are present in the control culture. It is desireable that at least 5 cells or clumps of cells/HPF be present to ensure adequate control culture growth. The importance of establishing a standard control growth is to provide a basis for determining relative cell growth inhibition or stimulation in the presence of estrogen or the hydrazone.

After sufficient cell growth appears in the flasks, the medium and contents are poured out and the slide bottom peeled off using the SlideFlask opener as shown in FIG. 1. The slides, which have previously been labelled A-E, are air dried for a few minutes and sprayed with a cytofixative (Pro-Fixx TM, Lerner Labs) then examined under a conventional light microscope as any cytological or histological slides would ordinarily be examined by one skilled in the art. If the laboratory has an inverted field microscope, the above slide preparation can be eliminated and the flasks containing cells and liquid content can be counted directly, without preparing and staining the slides. High power fields are scanned, counted and compared in all five tissue culture systems (Flasks A-E). Ten (10) cells/HPF arbitrarily is considered 100% growth, because sufficient cell growth in the control culture was set at 10 cells/HPF. Results from each of the two corresponding flasks are averaged.

One object of the assay is to find the lethal dose of hydrazones that inhibit 50% of the cells from growing. This dose is referred to as the $IC_{50}$, and is present when there are 5 or fewer cells/HPF (compared to the 10 cells/HPF control). Another object is to determine the cell growth response to 10 μg/ml estradiol in the culture medium. These results, both separately and together, provide important information about the receptor status of the cells and the likely response of the patient to hormonal or non-hormonal therapy.

The results of the assay are interpreted as follows:
1. Patients whose cancer cells in flask B (in the presence of 10 μg/ml estradiol) that have ≦50% growth ($IC_{50}$) as compared to control, are considered sensitive to estrogens and are candidates for antiestrogen therapy.
2. If estradiol ($E_2$) in flask B either has no influence or stimulates cell growth, the tumor cells are considered not to be estrogen sensitive. This is paradoxical because growth of the estrogen sensitive cells would be expected to be stimulated by estradiol. Instead, growth stimulation here signals probable unresponsiveness to therapeutic estrogen deprivation. This paradoxical result is believed to be strictly an in vitro phenomenon. The high estrogen content of the flask (μg/ml) as compared to (ng/ml) physiological concentrations of estrogen in the body apparently is responsible for this inhibition.
3. If the cell growth is inhibited by exposure to estrogens in flask B, then an $IC_{50}$ should also be observed in flasks C and D with A-007. If the cells are 100% sensitive to estradiol (no cell growth in flask B) and completely inhibited by low concentrations of A-007 (no growth in flask C), the patient should be treated by an antiestrogen therapy. Examples of such therapy include tamoxifen, A-007, glutethimide, or surgical removal of the ovaries or adrenal glands.
4. If an $IC_{50}$ is noted in flask B as well as in flasks C (A-007, 10 μg/ml) or D (A-007, 15 μg/ml), the cells should be considered sensitive to non-hormonal cancer chemotherapy, as well as antiestrogen therapies. Examples of non-hormonal cancer chemotherapy include the CMF regimen (cyclophosphamide, methotrexate and 5-fluorouracil) as well as A-007 at cytotoxic doses.
5. If the cells only show $IC_{50}$ inhibition in flask C (A-007, 10 μg/ml) or D (A-007, 15 μg/ml), but not in flask B (with estradiol), the cells should be considered sensitive only to non-hormonal chemotherapy.
6. If the cells only show inhibition in flask E (A-007, 20 μg/ml) and are not inhibited by estradiol (flask A), the cells are considered poorly sensitive to both antiestrogens and other types of chemotherapy.
7. For cells such as colon and other cancers that are not dependent on estrogens for growth, flask B may be eliminated from use in the test system.

Antiestrogenic/Cytotoxic Activities

The use of estrogen and progesterone receptors to predict sensitivities of breast cancer to antiestrogen therapy has been a major step forward in cancer management, as recounted by McGuire, et al., Cancer Res. 37:637–9 (1977); Powell, et al., Cancer Res. 39:1678–82 (1979); Clark, et al., Semin Oncol; 125:Suppl 1:20–5 (1988). Unfortunately, information regarding chemotherapy sensitivities and prognosis cannot be obtained from these studies.

In accordance with the present invention, cancer cells are grown under physiological conditions to document viability and growth patterns. In the case of breast and ovarian cancers, which contain ER and PgR in up to 55% and 20% of cases, the influence of μg/ml of estradiol are assayed. Natural estradiol and other estrogens in ng/ml quantities or less can stimulate the growth and replication of ER positive breast cancer resulting in well-defined stellate cells. Paradoxically μg/ml concentrations of estradiol inhibit breast cancer growth. Breast cancer cells that are estrogen sensitive are stellate types of cells. The estrogen independent cells are small undifferentiated cells. The sensitivities of all the cultured tissues to A-007 or one of the described hydrazones are evaluated.

The in vitro data for breast cancer, ovarian cancer and colon cancer are provided in Tables II, III and IV. This data illustrates that even though agents other than the hydrazones are not routinely included in the culture assays, the use of A-007 predicts patient response to agents such as doxorubicin and 5-fluorouracil (5-FU).

The data regarding results from breast cancer testing are:

TABLE II

| | | | Breast Cancer Cases | | |
|---|---|---|---|---|---|
| Specimen | E-R* (+>19) | Pg-R* (+>10) | Control** (Flask A) | $E_2$*** (10 μg/ml) | A-007 (μg/ml)*** $IC_{50}$ |
| 1 | <4 | <3 | 100% | 100% | 5 |
| 2 | 54 | 43 | 50% | 10% | 1 |
| 3 | 82 | 346 | 0% | 30% | 3 |

TABLE II-continued

Breast Cancer Cases

| Specimen | E-R* (+>19) | Pg-R* (+>10) | Control** (Flask A) | $E_2$*** (10 μg/ml) | A-007 (μg/ml)*** $IC_{50}$ |
|---|---|---|---|---|---|
| 4 | 59 | 378 | 75% | 10% | 3 |
| 5 | 121 | 179 | 100% | 20% | 3 |
| 6 | 82 | 289 | 100% | 100% | <5 |
| 7 | 796 | 3418 | 10% | 0% | <1 |
| 8 | 440 | 998 | 100% | 10% | 5 |
| 9 | 62 | 67 | 100% | 10% | 3 |
| 10 | 35 | 80 | 85% | 10% | 4 |
| 11 | 289 | 256 | 75% | 65% | 3 |
| 12 | >450 | 89 | 10% | 90% | 3 |
| 13 | 171 | 497 | 50% | 5% | 3 |
| 14 | 214 | 201 | 50% | 90% | 2 |
| 15 | 9 | 14 | 35% | 100% | <1 |
| 16 | <5 | <3 | 100% | 100% | 10 |
| 17 | 30 | <3 | 100% | 100% | 10 |
| 18 | <5 | <3 | 100% | 90% | 12 |
| 19 | <4 | <3 | 100% | 100% | 15 |
| 20 | <5 | <3 | 90% | 87% | 15 |
| 21 | <5 | <3 | 100% | 100% | 15 |
| 22 | 73 | 57 | 100% | 100% | 12 |
| 23 | 19 | 7 | 100% | 95% | 15 |
| 24 | <3 | <5 | 100% | 100% | >10 |
| 25 | | | | | |
| 26 | 17 | 45 | 100% | 100% | 20 |
| 27 | <5 | <3 | 100% | 100% | 17 |
| 28 | 16 | 106 | 50% | 65% | 18 |
| 29 | <5 | <3 | 100% | 80% | >20 |

*ER and PgR: Receptor values in fmol/μg protein; ER > 5 and PgR > 3 are considered positive for estrogen sensitivity by most laboratories.
**Control: 10 cells or clumps/HPF = 100% growth
***Estradiol: 10 cells or clumps/HPF = 100% growth
****$IC_{50}$: Conc. of A-007 or another hydrazone required to inhibit 50% of cancer cell growth.

Data regarding ovarian cancer cells are:

TABLE III

Ovarian Cancer Cells

| Specimen | Control* (Flask A) Growth | $E_2$** (10 μg/ml) Growth | A-007 (μg/ml)*** $IC_{50}$ |
|---|---|---|---|
| 30 | 100% | 100% | 17 |
| 31 | 100% | 95% | 10 |
| 32 | 60% | 55% | 8 |
| 33 | 50% | 50% | 7 |
| 34 | 30% | 25% | 18 |
| 35 | 100% | 90% | 15 |
| 36 | 100% | 100% | 15 |
| 37 | 0% | 100% | 15 |
| 38 | 100% | 100% | 17 |
| 39 | 100% | 100% | 12 |
| 40 | 100% | 100% | 7 |
| 41 | 100% | 100% | 6 |

*Control: 10 cells or clumps/HPF = 100% growth
**Estradiol: 10 cells or clumps/HPF = 100% growth
***$IC_{50}$: Conc. of A-007 or another hydrazone required to inhibit 50% of cancer cell growth.

Data regarding inhibition of colon cancer cells in the test system is presented in TABLE IV:

TABLE IV

Colon Cancer Cells

| Specimen | Control* (Flask A) | A-007 (μ/ml)** $IC_{50}$ |
|---|---|---|
| 42 | 100% | 6 |
| 43 | 100% | 7 |
| 44 | 100% | 6 |
| 45 | 100% | 15 |
| 46 | 100% | >20 |
| 47 | 100% | >20 |
| 48 | 50% | 17 |
| 49 | 100% | >20 |
| 50 | 100% | >20 |
| 51 | 100% | 17 |
| 52 | 100% | 15 |

*Control: 10 cells or clumps/HPF = 100% growth
**$IC_{50}$: Conc. of A-007 or another hydrazone required to inhibit 50% of cell growth.

METHOD OF USE OF THE TEST SYSTEM

Breast Cancer

Case 1 (Specimen 22):

A 73 year old white female with advanced breast cancer that was already metastatic to bone had ER/PgR values of 73/57. These values would conventionally be taken to indicate that the tumor is estrogen dependent, hence the patient was treated with the antiestrogenic drug tamoxifen. Her tumor enlarged, however, while on tamoxifen therapy, and she required chemotherapy (doxorubicin, 5-fluorouracil and cyclophosphamide). On chemotherapy, the patient's condition improved. Her tumor tissue's $IC_{50}=12$ with A-007 and growth in estradiol was 100%. Hence these values would have predicted that her tumor would be insensitive to treatment with an antiestrogen (such as tamoxifen) but would respond to cytotoxic agents such as doxorubicin, 5-fluorouracil and/or cyclophosphamide. It is notable that inhibition of cell growth in the presence of A-007 does not merely predict tumor sensitivity to A-007, but instead is a marker for sensitivity to cytotoxic agents.

Case 2 (Specimen 26):

A 76 year old black female with advanced breast cancer had an ER/PgR of 17/45 and tumor spread to the chest wall. In view of her "positive" receptor status, she was treated with tamoxifen and did not respond. Patient 26 was then treated with 5-fluorouracil, methotrexate and cyclophosphamide. She did not respond and expired. Her tissue results indicated no response to estrogens or to chemotherapy. This outcome would have been predicted (in spite of her "positive" receptor status) by an $IC_{50}=20$ in A-007 and no growth suppression by estradiol. Hence the method of the present invention could have predicted a poor prognosis, in advance of chemotherapy, that may have averted an unfruitful course of drug treatment with its attendant side effects. This contrasts with the prior art approach of treating all "receptor positive" patients with hormone and/or chemotherapy.

Case 3 (Specimen 16):

A 68 year old white female had severe breast cancer spread to her chest wall and lung and a "negative" receptor status (ER/PgR <5/3). Her tissue demonstrated no growth inhibition to estradiol and an $IC_{50}$ of 10 μg/ml in A-007. The absence of growth inhibition in estradiol confirms the negative receptor status, but an $IC_{50}$ μg/ml in A-007 predicted absence of multi-drug resistance to cytotoxic agents. This patient was treated with doxorubicin and had a complete response that has lasted for six months.

Case 4 (Specimen 27):

A 66 year old white female with breast cancer spread to axillary lymph nodes was not considered a candidate for tamoxifen (ER/PgR= <5/<3). She was treated with cyclophosphamide, methotrexate and 5-fluorouracil post surgery. She failed with aggressive recurrence in ten months and expired. Her tissue demonstrated an $IC_{50}=17$ for A-007 and no growth inhibition in the presence of estradiol. The test assays would have predicted multi-drug resistance to cytotoxic agents, as was observed in fact.

Ovarian Cancer

Case 5 (Specimen 31):

A 65 year old female with advanced ovarian cancer spread to the abdomen was treated with doxorubicin. She had an impressive response after one treatment. Her tissue had an $IC_{50}=10$ in A-007, but only 5% growth inhibition in the presence of $E_2$. Hence a trial of antiestrogen therapy would have probably been unsuccessful, while the low $IC_{50}$ predicted the response to doxorubicin and other agents.

Case 6 (Specimen 33):

A 65 year old black female with advanced unresectable ovarian cancer was treated with paraplatin (Carboplatin). She has undergone a complete remission and is doing well. Her cancer tissue had an $IC_{50}$ of 7 in A-007, but no growth inhibition was observed with $E_2$ (the 50% growth with $E_2$ was the same as the 50% growth in control flask A). The low $IC_{50}$ with A-007 predicted response to non-hormonal chemotherapy.

Case 7 (Specimen 30):

A 68 year old white female with advanced ovarian cancer was treated aggressively with doxorubicin and paraplatin (Carboplatin) with no response and she expired. Her tissue had an $IC_{50}=17$ in A-007 and was not inhibited by estradiol. These tissue findings support the treatment outcome, which was characterized by multidrug resistance.

Colon Cancer

Case 8 (Specimen 48):

A 50 year old white male with advanced colon cancer was treated with 5-fluorouracil. His tumor did not demonstrate any response and required exploration and surgery. His tissue demonstrated an $IC_{50}=17$ in A-007. This relatively high $IC_{50}$ is consistent with multi-drug resistance to cytotoxic agents.

Case 9 (Specimen 43):

A 75 year old white female with advanced colon cancer was treated with 5-fluorouracil and has done well. Her cancer tissue demonstrated an $IC_{50}=7$ in A-007, which is consistent with her observed response to the cytotoxic agent. Hence the $IC_{50}$ of A-007 predicts tumor susceptibility to agents other than A-007.

A-007 and the other disclosed nitrophenylhydrazones are useful in confirming sensitivity to antiestrogenic agents that is separately suggested by culture inhibition in the presence of μg/ml concentrations of estradiol. The nitrophenylhydrazones are also helpful in predicting tumor response to non-hormonal cytotoxic agents. This dual predictive capacity is believed to be due to the hydrazones' bipotential effect on tumor cells. These hydrazones demonstrate both an antiestrogenic mechanism of action at lower doses and a direct cytotoxic action at higher doses. The direct cytotoxic action begins to predominate at concentrations of 10 μg/ml for A-007.

Definitions

In summary, the foregoing examples and data illustrate a method of predicting response of a tumor patient to therapy. As used herein, the term "tumor patient" refers to a person having a neoplasm, particularly a malignant neoplasm and, in most especially preferred embodiments, a hormone dependent neoplasm, such as ovarian or breast cancer. In one embodiment, the method includes culturing a first sample of the cells in the presence of a sufficient amount of an estrogen to inhibit growth of estrogen sensitive cells in the culture. The term "culturing" implies that the first sample includes a culture medium suitable for allowing growth of the tumor cells, such as RPMI-1640 containing 10% FBS 100 μg/ml streptomycin and 100 units/ml penicillin. The term "sufficient amount of an estrogen to inhibit growth of estrogen sensitive cells" refers to an amount of estrogen which decreases the number of cells per high power field to below the number of cells/HPF observed in a control culture.

A second sample of the cells is cultured in the presence of a sufficient amount of a cancer chemotherapeutic agent to inhibit growth of cells sensitive to the agent. As used herein, a cancer chemotherapeutic agent includes any drug useful in treating malignant neoplasms, and includes such substances as methotrexate, vincristine, 5-fluorouracil, cis-diamminedichloroplatinum, doxorubicin, cyclophosphamide and others. Inhibition of cell growth, in this context, is determined by a reduction in the number of cells compared to a control. In one specific embodiment disclosed herein, wherein the control contains 10 cells/HPF, inhibition is indicated by a reduction of cell number to less than 10 cells/HPF, most preferably less than 5 cells/HPF.

The degree of inhibition of cell growth in each cultured sample is quantitated in accordance with this method. Such quantitation can take the form of counting the number of cells per high power field in each cultured sample. A particularly useful form of quantitation is to determine the $IC_{50}$ of each sample, or the dose needed to inhibit the growth of ≧50% of the cells.

The term "estrogen" refers to a substance that tends to promote estrus and stimulate the development of female secondary sexual characteristics. Included in the scope of this term are estradiol, estrone, estriol, and other substances. In particular disclosed embodiments, cells are exposed to supraphysiologic amounts of estradiol in culture to determine tumor cell sensitivity to antiestrogenic drugs. Supraphysiologic amounts are those above the basal level seen in a normal human female. An example of a supraphysiologic amount is a concentration in the (μg/ml) range, or greater. Supraphysiologic amounts of estrone, estriol or other estrogens are easily determined, and their inhibitory concentrations in culture with estrogen dependent tumor cells are easily determined without undue experimentation.

The assay of the present invention preferably employs a chemotherapeutic agent that has antiestrogenic properties, such as tamoxifen. More preferably, the antiestrogenic agent also has cytotoxic properties, as with the nitrophenylhydrazones of some embodiments of the present invention. Antiestrogenic properties refer to an ability to interfere with the interaction between estrogen and estrogen receptors in cells. Cytotoxic properties refer to a specific toxic action upon a cell, and not merely interference with interaction between an estrogen receptor and its ligand.

The present method further includes selecting a treatment modality based on the degree of inhibition of cell growth in culture. The term "selecting a treatment" can refer to a broad variety of activities, including recommending a course of treatment or actually treating a patient with a particular therapeutic modality. The term "treatment modality" includes such things as drug therapy, surgical therapy (for example, adrenalectomies and oophorectomies) or even refraining from treatment in cases of poor treatment prognosis. The term "antiestrogen therapy" refers to using antiestrogenic drugs (such as tamoxifen or nitrophenylhydrazones, or adrenal cortical suppressors such as glutethimide), or surgical interventions such as oophorectomies or adrenalectomies.

Antiestrogen therapies are selected, in accordance with some embodiments of this invention, when the degree of inhibition of cell growth in the estrogen exposed sample is significant. Significant inhibition, in this context, refers to an inhibition of at least about 50%, or 5 or less cells/HPF compared to a 10 cell/HPF control. If cell growth in the estrogen exposed sample is stimulated or not inhibited, something other than an antiestrogen therapy is selected. Examples of such other therapies include doxorubicin, 5-FU, methotrexate, cyclophosphamide and other drugs which are not known solely to interfere with estrogen receptors as a principal mechanism of action. Antiestrogen therapy also includes treatment with drugs, such as A-007 and other nitrophenylhydrazones, that possess both antiestrogenic properties and direct cytotoxic activity. Differential exhibition of antiestrogenic and cytotoxic properties may occur at different dosage ranges, for example, a cytotoxic mechanism of action may predominate at higher doses while an antiestrogenic mechanism may be most evident at lower doses.

In other embodiments, an antiestrogen treatment modality is selected if the degree of inhibition of cell growth in both the estrogen exposed and drug exposed culture is substantially complete. A substantially complete degree of inhibition is, for example, at least a 50% inhibition, most preferably 90–100% inhibition.

In other embodiments of the invention, either an antiestrogenic or non-hormonal therapy is provided for the patient if cell growth in the first and second sample is partially inhibited. The term "partially inhibited" refers to an inhibition below the level of growth seen in the control culture. Such inhibition is at least about 10%, preferably at least about 50%, or between 10% and 50%.

A disclosed embodiment of the invention uses A-007 in culture concentrations of 10 μg/ml, 15 μg/ml and 20 μg/ml. These culture concentrations are "calibrated" such that an $IC_{50}$ at 10 μg/ml indicates a high degree of tumor susceptibility to a broad variety of chemotherapeutic agents. An $IC_{50}$ at 15 μg/ml indicates an intermediate likelihood of response to chemotherapy, while an $IC_{50}$ above 15 μg/ml suggests multi-drug resistance and a poor prognosis, even with chemotherapy. It is a particular advantage of A-007 that it is so finely calibrated to predict therapeutic outcome. These precise calibrations, if they exist, have not yet been found for some of the other hydrazones or other chemotherapeutic agents, such as doxorubicin or methotrexate. Grosser indications of culture growth inhibitions are used with these agents, for example any inhibition of growth compared to controls. The method is still useful with these other drugs, but A-007 is a particularly preferred embodiment because of its high degree of calibration.

The antiestrogenic hydrazones (of which A-007 is a paradigm) contain substituents $R^1$, $R^2$ and X. $R^1$ is preferably a water soluble group, and can include hydrogen, hydroxy, succinate, esters or other hydrophilic groups or hydrogen bonding groups. Substituent $R^2$ is a phenyl or substituted phenyl, preferably a hydroxy or ester substituted phenyl, wherein the ester substitution is preferably acetate or succinate. Substituent X is phenyl or substituted phenyl, wherein X is preferably nitro or dinitro substituted.

Having illustrated and described the principles of the invention in a preferred embodiment, it should be apparent to those skilled in the art that the invention can be modified in arrangement in detail without departing from such principles. I claim all modifications coming within the spirit and scope of the following claims.

I claim:

1. An in vitro method of predicting response of a tumor to therapy in vivo, comprising the steps of:
   culturing a first sample of tumor cells in the presence of a sufficiently supraphysiological amount, which is about 10 μg/ml or more, of an estrogen to inhibit growth in the culture of estrogen-sensitive cells from a tumor which requires estrogen for growth;
   culturing a second sample of the cells in the presence of a sufficient amount of an antiestrogenic hydrazone to inhibit growth of cells sensitive to the agent;
   quantitating the degree of inhibition of cell growth in each cultured sample;
   selecting an antiestrogen therapy for subjects whose first cultured sample has an $IC_{50}$ less than or equal to 10 μg/ml; and
   selecting a non-hormonal chemotherapy if cell growth is at least partially inhibited in a second sample, but not substantially inhibited in the first sample.

2. The method of claim 1 wherein the estrogen is selected from the group consisting of estradiol, estrone, and estriol.

3. The method of claim 2 wherein the antiestrogenic hydrazone is an antiestrogenic agent having cytotoxic properties.

4. The method of claim 3 wherein the antiestrogenic agent is a nitrophenylhydrazone.

5. The method of claim 4 wherein the nitrophenylhydrazone is:

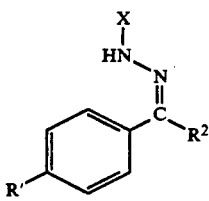

wherein $R^1$ is selected from the group consisting of H, OH, $CH_3COO$, or $HO_2C(CH_2)_2COO$, $R^2$ is $C_6H_4OH$, $C_6H_4OCOCH_3$, $C_6H_4OOC(CH_2)_2CO_2H$ or $C_6H_5$, and X is $C_6H_5$, $C_6H_4$-4$(NO_2)$, $C_6H_4$-3$(NO_2)$, or $C_6H_3$-2,4$(NO_2)_2$.

6. The method of claim 5 wherein $R^2$ is a hydroxy or ester substituted phenyl.

7. The method of claim 5 wherein X is $C_6H_4$-4$(NO_2)$ or $C_6H_4$-3$(NO_2)$.

8. The method of claim 5 wherein X is $C_6H_3$-2,4$(NO_2)_2$.

9. The method of claim 1 wherein the step of culturing the second sample comprises culturing the second sample in the presence of varying amounts of the hydrazone.

10. A method of selecting treatment for a subject having a breast, ovarian, or colon tumor, comprising the steps of:
culturing a first sample of cells from the tumor in the presence of 10 µg/ml estradiol;
culturing a second sample of cells from the tumor in the presence of a hydrazone having the formula

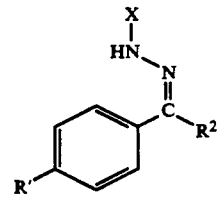

wherein $R^1$ is selected from the group consisting of H, OH, $CH_3COO$, or $HO_2C(CH_2)_2COO$, $R^2$ is $C_6H_4OH$, $C_6H_4OCOCH_3$, $C_6H_4OOC(CH_2)_2CO_2H$ or $C_6H_5$, and X is $C_6H_5$, $C_6H_4$-4$(NO_2)$, $C_6H_4$-3$(NO_2)$, or $C_6H_3$-2,4$(NO_2)_2$;
selecting an antiestrogen therapy for subjects whose first cultured sample has an $IC_{50}$ less than or equal to 10 µg/ml; and
selecting a non-hormonal chemotherapy if cell growth is at least partially inhibited in the second sample, but not substantially inhibited in the first sample.

* * * * *

UNITED STATES PATENT AND TRADEMARK OFFICE
CERTIFICATE OF CORRECTION

PATENT NO. : 5,270,172

DATED : December 14, 1993

INVENTOR(S) : Lee R. Morgan

It is certified that error appears in the above-identified patent and that said Letters Patent is hereby corrected as shown below:

Column 3, line 24, delete "R'" and substitute therefor --$R^1$--.

Column 4, line 62, delete "R'" in the structural drawing and substitute therefor --$R^1$--.

Please substitute the attached Table I and Table II for Table I printed in column 8 and Table II printed in column 15.

Column 15, line 18, delete "R'" in the structural formula and substitute therefor --$R^1$--.

Column 16, line 19, delete "R'" in the structural formula and substitute therefor --$R^1$--.

UNITED STATES PATENT AND TRADEMARK OFFICE
CERTIFICATE OF CORRECTION

PATENT NO. : 5,270,172
DATED : December 14, 1993
INVENTOR(S) : Lee R. Morgan

It is certified that error appears in the above-indentified patent and that said Letters Patent is hereby corrected as shown below:

TABLE I

Antiestrogenic Hydrazones

| Compound | $R^1$ | $R^2$ | X |
|---|---|---|---|
| A-007 | HO | $C_6H_4OH$ | $C_6H_3-2,4(NO_2)_2$ |
| A-070 | HO | $C_6H_4OH$ | $C_6H_5$ |
| A-100 | HO | $C_6H_4OH$ | $C_6H_4-4(NO_2)$ |
| A-034 | HO | $C_6H_4OH$ | $C_6H_4-3(NO_2)$ |
| A-032 | $CH_3COO$ | $C_6H_4OCOCH_3$ | $C_6H_3-2,4(NO_2)_2$ |
| A-033 | H | $C_6H_5$ | $C_6H_3-2,4(NO_2)_2$ |
| A-106 | $HO_2C(CH_2)_2COO$ | $C_6H_5-OOC(CH_2)_2CO_2H$ | $C_6H_3-2,4(NO_2)_2$ |

UNITED STATES PATENT AND TRADEMARK OFFICE
CERTIFICATE OF CORRECTION

PATENT NO. : 5,270,172
DATED : December 14, 1993
INVENTOR(S) : Lee R. Morgan

It is certified that error appears in the above-indentified patent and that said Letters Patent is hereby corrected as shown below:

Breast Cancer Cases

| Specimen | $ER^*$ (+>19) | $PgR^*$ (+>10) | Control** (Flask A) | $E_2$*** (10 μg/ml) | $\dfrac{\text{A-007 (μg/ml)}^{***}}{IC_{50}}$ |
|---|---|---|---|---|---|
| 1 | <4 | <3 | 100% | 100% | 5 |
| 2 | 54 | 43 | 50% | 10% | 1 |
| 3 | 82 | 346 | 0% | 30% | 3 |
| 4 | 59 | 378 | 75% | 10% | 3 |
| 5 | 121 | 179 | 100% | 20% | 3 |
| 6 | 82 | 289 | 100% | 100% | <5 |
| 7 | 796 | 3418 | 10% | 0% | <1 |
| 8 | 440 | 998 | 100% | 10% | 5 |
| 9 | 62 | 67 | 100% | 10% | 3 |
| 10 | 35 | 80 | 85% | 10% | 4 |
| 11 | 289 | 256 | 75% | 65% | 3 |
| 12 | >450 | 89 | 10% | 90% | 3 |

Table II

UNITED STATES PATENT AND TRADEMARK OFFICE
CERTIFICATE OF CORRECTION

PATENT NO. : 5,270,172

DATED : December 14, 1993

INVENTOR(S) : Lee R. Morgan

It is certified that error appears in the above-indentified patent and that said Letters Patent is hereby corrected as shown below:

| 13 | 171 | 497 | 50% | 5%   | 3   |
|----|-----|-----|-----|------|-----|
| 14 | 214 | 201 | 50% | 90%  | 2   |
| 15 | 9   | 14  | 35% | 100% | <1  |
| 16 | <5  | <3  | 100%| 100% | 10  |
| 17 | 30  | <3  | 100%| 100% | 10  |
| 18 | <5  | <3  | 100%| 90%  | 12  |
| 19 | <4  | <3  | 100%| 100% | 15  |
| 20 | <5  | <3  | 90% | 87%  | 15  |
| 21 | <5  | <3  | 100%| 100% | 15  |
| 22 | 73  | 57  | 100%| 100% | 12  |
| 23 | 19  | 7   | 100%| 95%  | 15  |
| 24 | <3  | <5  | 100%| 100% | >10 |
| 25 | 65  | 12  | 50  | 65   | 15  |
| 26 | 17  | 45  | 100%| 100% | 20  |
| 27 | <5  | <3  | 100%| 100% | 17  |
| 28 | 16  | 106 | 50% | 65%  | 18  |
| 29 | <5  | <3  | 100%| 80%  | >20 |

ER & PgR: Receptor values in fmol/μg protein; ER > 5 and PgR > 3 are considered positive for estrogen sensitivity by most laboratories.
*Control: 10 cells or clumps/HPF = 100% growth
**Estradiol: 10 cells or clumps/HPF = 100% growth
$IC_{50}$: Conc. of A-007 or another hydrazone required to inhibit 50% of cancer cell growth.

Signed and Sealed this

Eighth Day of November, 1994

Attest:

BRUCE LEHMAN

Attesting Officer          Commissioner of Patents and Trademarks